United States Patent
Vargas

(10) Patent No.: US 7,740,886 B1
(45) Date of Patent: Jun. 22, 2010

(54) BEDSORE TREATMENT OINTMENT

(76) Inventor: Sara Vargas, 18012 Telechron Ave., Whittier, CA (US) 90605

(*) Notice: Subject to any disclaimer, the term of this patent is extended or adjusted under 35 U.S.C. 154(b) by 11 days.

(21) Appl. No.: 12/171,396

(22) Filed: Jul. 11, 2008

(51) Int. Cl.
- A61K 36/886 (2006.01)
- A61K 36/81 (2006.01)
- A61K 36/13 (2006.01)
- A61K 36/00 (2006.01)

(52) U.S. Cl. .............. 424/744; 424/778; 424/770; 424/742

(58) Field of Classification Search .......... None
See application file for complete search history.

(56) References Cited

U.S. PATENT DOCUMENTS

| | | | |
|---|---|---|---|
| 4,294,852 A | 10/1981 | Wildnaner | |
| 4,960,592 A * | 10/1990 | Hagen et al. | 424/537 |
| 5,407,670 A | 4/1995 | Shinault | |
| 5,795,573 A | 8/1998 | Paradise | |
| 5,879,688 A | 3/1999 | Coury et al. | |
| 5,976,547 A | 11/1999 | Archore et al. | |
| 6,194,455 B1 | 2/2001 | Wharton | |
| 2003/0224071 A1* | 12/2003 | Murad | 424/728 |
| 2004/0157766 A1* | 8/2004 | Embil et al. | 514/1 |
| 2007/0065527 A1* | 3/2007 | Medvedev et al. | 424/736 |

* cited by examiner

Primary Examiner—Christopher R. Tate
Assistant Examiner—Deborah A. Davis

(57) ABSTRACT

A bedsore treatment ointment comprises a mixture including aloe vera, arnica, eucalyptus oil, pine oil, methyl salicylate, phenol, and lanolin. The mixture is positioned on bedsores for the treatment thereof.

6 Claims, 1 Drawing Sheet

| INGREDIENTS | AMOUNT |
|---|---|
| ALOE VERA | 2 mg |
| ARNICA | 2 mg |
| EUCALYPTUS OIL | 2 mg |
| TREMENTI OIL | 2 mg |
| PHENOL | 3.5 mg |
| LANOLIN | 100 mg |
| METHYL SALICYLATE | 2 mg |

BEDSORE TREATMENT OINTMENT

BACKGROUND OF THE INVENTION

1. Field of the Invention

The present invention relates to bedsore remedies and more particularly pertains to a new bedsore remedy for treating bedsores and decreasing the amount of healing time for the bedsores.

2. Description of the Prior Art

The use of bedsore remedies is known in the prior art. While these devices fulfill their respective, particular objectives and requirements, the need remains for a new remedy which decreases the amount of time required to heal a bedsore and which prevents the spreading of bedsores.

SUMMARY OF THE INVENTION

The present invention meets the needs presented above by generally comprising a mixture including aloe vera, arnica, eucalyptus oil, pine oil, methyl salicylate, phenol, and lanolin. The mixture is positioned on bedsores for the treatment thereof.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 2:
FIG. 2 is a listing of the ingredients the present invention.
Figure 1:
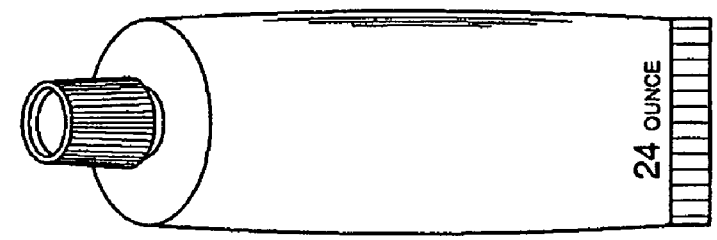
FIG. 1 is a front view of containers of a bedsore treatment ointment according to the present invention.
Figure 1:

With reference now to the drawings, and in particular to FIGS. 1 and 2 thereof, a new bedsore remedy embodying the principles and concepts of the present invention and generally designated by the reference numeral 10 will be described.

As best illustrated in FIGS. 1 and 2, the bedsore treatment ointment 10 generally comprises a mixture including by weight between 1 percent and 3 percent aloe vera, between 1 percent and 3 percent arnica, between 1 percent and 3 percent eucalyptus oil, between 1 percent and 3 percent pine oil, between 1 percent and 3 percent methyl salicylate, between 2 percent and 4 percent phenol, and between 80 percent and 90 percent lanolin.

More specifically, the mixture includes by weight between 1.5 percent and 2 percent aloe vera, between 1.5 percent and 2 percent arnica, between 1.5 percent and 2 percent eucalyptus oil, between 1.5 percent and 2 percent pine oil, between 1.5 percent and 2 percent methyl salicylate, between 2.5 percent and 3.5 percent phenol, and between 85 percent and 90 percent lanolin.

An example of a specific mixture includes:

2 mg aloe vera gel;
2 mg arnica (extract of arnica blossoms);
2 mg eucalyptus oil;
2 mg pine oil;
2 mg methyl salicylate;
3.5 mg phenol; and
100 mg lanoline.

In particular, the pine oil to be used is distilled from the sap of the *Pinus edulis* pine tree, which is native to the states of New Mexico and Arizona and can be found throughout the United States Southwest. This oil is often referred to as "Trementina Oil" which is a generic Spanish term for "turpentine" but which has been used specifically for oil, sap and resin derived from the *Pinus edulis*, commonly referred to as the Piñon Tree. One distributor of this oil, under the name of "Pinon Essential Oil," is The Water Box Co., LLC, 1816 Murray Avenue, Waukesha, Wis. 53186. Another such distributor is Distribuidora Remeke SA de CV 1 de Mayo No. 2000 Col. Santa Rita CP, 31020, Chihuahua, Chihuahua, Mexico.

The mixture, once made, is preferable placed in an air impermeable container 12. When used, the mixture is positioned on a bedsore, or decubitus ulcer, and may be then covered with a bandage. The mixture offers relief to a patient suffering from bedsores, prevents the enlargement of the treated bedsores and heals the bedsores.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An ointment for treating bedsores, said ointment comprising:

a mixture including, by weight, between 1 percent and 3 percent aloe vera, between 1 percent and 3 percent arnica, between 1 percent and 3 percent eucalyptus oil, between 1 percent and 3 percent pine oil, between 1 percent and 3 percent methyl salicylate, between 2 percent and 4 percent phenol, and between 80 percent and 90 percent lanolin; and wherein said mixture is positionable on a bedsore.

2. The ointment according to claim 1, wherein said pine oil is derived from the *Pinus edulis* tree.

3. An ointment for treating bedsores, said ointment comprising:

a mixture including, by weight, between 1.5 percent and 2 percent aloe vera, between 1.5 percent and 2 percent arnica, between 1.5 percent and 2 percent eucalyptus oil, between 1.5 percent and 2 percent pine oil, between 1.5 percent and 2 percent methyl salicylate, between 2.5 percent and 3.5 percent phenol, and between 85 percent and 90 percent lanolin; and wherein said mixture is positionable on a bedsore.

4. The ointment according to claim 3, wherein said pine oil is derived from the *Pinus edulis* tree.

5. An ointment for treating bedsores, said ointment comprising:

a mixture including aloe vera, arnica, eucalyptus oil, pine oil, methyl salicylate, phenol, and lanolin, said lanolin comprising at least ten times by weight each of the aloe vera, arnica, eucalyptus oil, pine oil, methyl salicylate and phenol; and wherein said mixture is positionable on a bedsore.

6. The ointment according to claim 5, wherein said pine oil is derived from the *Pinus edulis* tree.

\* \* \* \* \*